(12) United States Patent
Laine et al.

(10) Patent No.: US 6,927,301 B2
(45) Date of Patent: Aug. 9, 2005

(54) WELL-DEFINED NANOSIZED BUILDING BLOCKS FOR ORGANIC/INORGANIC NANOCOMPOSITES

(75) Inventors: Richard M. Laine, Ann Arbor, MI (US); Ryo Tamaki, Foster City, CA (US); Jiwon Choi, Ann Arbor, MI (US)

(73) Assignee: The Regents of The University of Michigan, Ann Arbor, MI (US)

( * ) Notice: Subject to any disclaimer, the term of this patent is extended or adjusted under 35 U.S.C. 154(b) by 211 days.

(21) Appl. No.: 10/069,640

(22) PCT Filed: Oct. 29, 2001

(86) PCT No.: PCT/US01/48451

§ 371 (c)(1),
(2), (4) Date: May 6, 2002

(87) PCT Pub. No.: WO02/100867

PCT Pub. Date: Dec. 19, 2002

(65) Prior Publication Data

US 2003/0120099 A1 Jun. 26, 2003

Related U.S. Application Data

(60) Provisional application No. 60/244,099, filed on Oct. 27, 2000.

(51) Int. Cl.⁷ .............................. C07F 7/04; C07F 7/21
(52) U.S. Cl. ....................... 556/450; 556/460; 556/461; 556/462
(58) Field of Search ................................ 556/450, 460, 556/461, 462

(56) References Cited

PUBLICATIONS

Feher et al, J. of Organometallic Chem, vol. 379, pp 33–40, 1989.*

J.F. Brown, Jr., et al., *Preparation and Characterization of the Lower Equilibrated Phenylsilsesquioxanes*, J. Am. Chem. Soc. 86 1120–1125 (1964).

M.G. Voronkov, et al., *Polyhedral Oligosilsesquioxanes and Their Homo Derivatives*, Top. Curr. Chem. 102, 199 (1982).

K. Olsson, et al., *On Octa– (Arylsilsesquioxanes). (ArSi)$_8$O$_{12}$ I. The Phenyl, 4–tolyl, and 1–naphthyl Compounds*, Arkiv. Kemi. 17 529–40 (1961).

* cited by examiner

*Primary Examiner*—Shailendra Kumar
(74) *Attorney, Agent, or Firm*—Brooks Kushman P.C.

(57) ABSTRACT

Functionalized silsesquioxanes containing from 6 to 24 silicon atoms and minimally about 67 mol percent $RSiO_{3/2}$ moieties where R is a phenyl group bearing a chemically reactive functional group are highly suitable for use as nanoparticles in producing highly ordered nanocomposites of many types, containing a high proportion of interphase. The nanocomposites have unusual physicochemical properties due to the use of uniform, highly functionalized nanoparticles.

4 Claims, 8 Drawing Sheets

WELL-DEFINED NANOSIZED BUILDING BLOCKS FOR ORGANIC/INORGANIC NANOCOMPOSITES

CROSS-REFERENCE TO RELATED APPLICATION

This application is the U.S. national phase of PCT application Ser. No. PCT/US01/48451, filed Oct. 29, 2001, which further claims the benefit of U.S. provisional application Ser. No. 60/244,099, filed Oct. 27, 2000.

STATEMENT REGARDING FEDERALLY SPONSORED RESEARCH OR DEVELOPMENT

The invention was made with Government support under FAA Contract No. 95-G-026 and U.S. Air Force, Phillips Laboratories. The Government has certain rights to the invention.

BACKGROUND OF THE INVENTION

1. Field of the Invention

The present invention pertains to functionalized, discrete silsesquioxanes which are useful, inter alia, for preparing organic and inorganic nanocomposites, to methods of their preparation and their use. Nanocomposites prepared from the functionalized silsesquioxanes have unusual physicochemical characteristics.

2. Background Art

Macroscopic composites of many types are known. Familiar examples include carbon fiber and glass fiber reinforced thermoplastic and thermoset composites. Composite properties generally exceed those predicted from application of the "rule-of-mixtures" based on the properties of the individual components. This increase in physicochemical properties is believed due to interfacial interactions between the dispersed and continuous phases. As the size of the various phases diminishes, the surface area increases, thus increasing the interfacial interactions. At the interfaces of divergent materials, a separate phase, the "interphase" can be hypothesized.

Nanocomposites are composites where the interphase characteristics dominate composite properties due to the very small size of the materials used to prepare the composites. The particles of nanocomposites may be viewed as having a maximum dimension of about 100 nm or less. While substances such as colloidal silica can be supplied in nanometer sizes, the functionality of such silica is limited, and the size and geometry of the individual particles are irregular. Thus, it is impossible to prepare nanocomposites having well defined nanostructural units from such products.

Cage-like silica compounds are known to exist. However, the functionality of such structures is generally limited to hydroxyl (silanol) functionality, if functionality is present at all, thus reducing their utility as nanocomposite building blocks.

Silsesquioxanes functionalized with —OSi(CH$_3$)$_2$H groups are known, as are poly(glycidyl) and similar derivatives prepared by hydrosilylating compounds such as allylglycidylether with the aforementioned Si—H functional silsesquioxanes. However, there is a need to provide additional reactive silsesquioxanes, particularly silsesquioxanes which exhibit high thermal stability and a wide variety of functionalization.

Octaphenylsilsesquioxanes ("OPS") have been known for some time, J. F. Brown, Jr., et al., J. AM. CHEM. SOC. 86 1120–1125 (1964), and are commercially available. OPS may be produced, for example, by the hydrolysis of phenylsilanes such as phenyltrichlorosilane and phenyltrimethoxysilane. However, the phenyl group itself is considered non-functional, and prior attempts to functionalize it have not proven successful. See, e.g. Voronkov, M. G., et al. "Polyhedral Oligosilsesquioxanes and Their Homo Derivatives," TOP. CURR. CHEM., 102, 199 (1982); and K. Olsson, et al., ARKIV. KEMI. 17 529–40 (1961). Olsson et al. were apparently successful in octanitrating octaphenyl silsesquioxane to form octakis(p-nitrophenyl)silsesquioxane in quantitative yield. However, the nitro group is an essentially unreactive group relative to use as a bonding group, and Olsson's attempts to reduce the octanitro compound to a useful and reactive octaamino compound were not successful, the authors describing the nitrophenyl-substituted compound as "inert."

It would be desirable to provide well defined, oligomeric silsesquioxanes which are functionalized with reactive groups which can be employed in controlled chemical bonding. If such functionalized silsesquioxanes were available, a variety of nanocomposites having well defined structure could be created. The resulting products could have numerous uses in fields as wide ranging as improved strength construction materials and photonic crystals or as traps for quantum dots, catalyst particles, etc., to name but a few.

SUMMARY OF THE INVENTION

The present invention pertains to functionalized, phenyl silsesquioxanes containing a minimum of six silicon atoms on average and having a maximum dimension of ≦100 nm, and containing preferably up to about 24 silicon atoms, these silsesquioxanes preferably having a cage like structure, or oligomeric or polymeric species derived by coupling such silsesquioxanes by Si—O—Si bonds. The phenyl silsesquioxanes have been functionalized with functional groups which may be used to link the silsesquioxanes to substrates or to other organic or inorganic compounds or structures to provide a vast array of nanocomposite materials.

DETAILED DESCRIPTION OF THE PREFERRED EMBODIMENTS

The functionalized silsesquioxanes of the present invention are limited to silsesquioxane structures being less than 100 nm in size in any dimension, and preferably having 24 or less silicon atoms ("macromonomers"), and to oligomeric or polymeric structures created by linking such silsesquioxanes together. By "silsesquioxanes" is meant a structure whose skeleton is composed substantially of $RSiO_{3/2}$ ("T") moieties. The silsesquioxanes of the present invention may contain less than 33 mol percent $R'_2SiO_{2/2}$ ("D") moieties, where R' may be R or may be a substantially non-reactive group such as an alkyl or aryl group. The amount of D moieties is preferably less than 10 mol percent, more preferably less than 5 mol percent. Most preferably, only incidental D moieties are present, and when present, generally define incompletely condensed corners of polyhedral structures. Some silicon atoms may be bonded to another silicon atom, or to another silicon atom by means of a bridging group such as —$CH_2$—, —$CH_2CH_2$— or aryl. However, the presence of such linkages is also incidental, in general. The majority of silicon atoms are bonded to other silicon atoms by Si—O—Si bonds.

Figure 1:
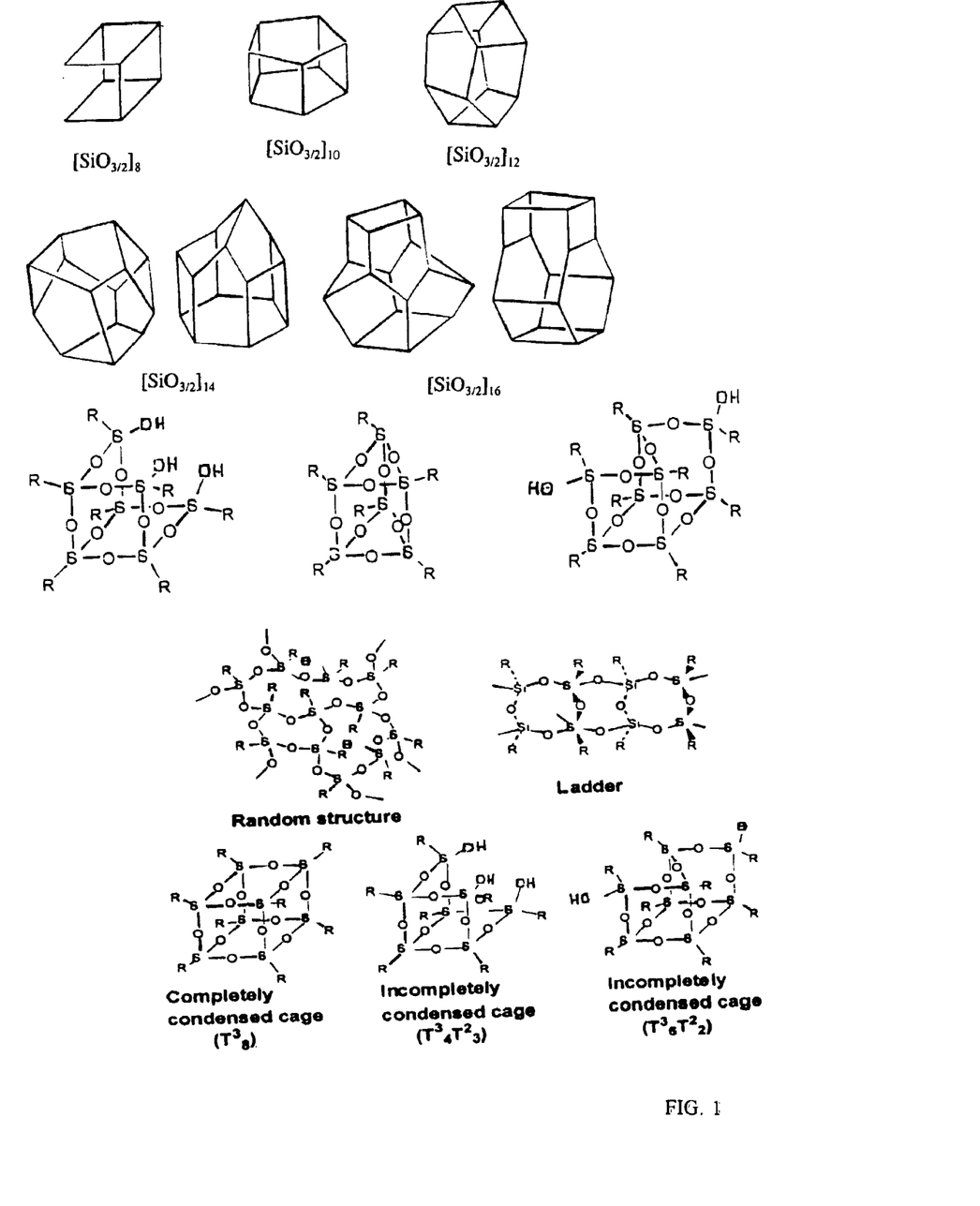
FIG. 1 illustrates in schematic form some of the silsesquioxane structures and functionalized silsesquioxane structures useful in the functionalized nanoparticles of the present invention.
Figure 2:
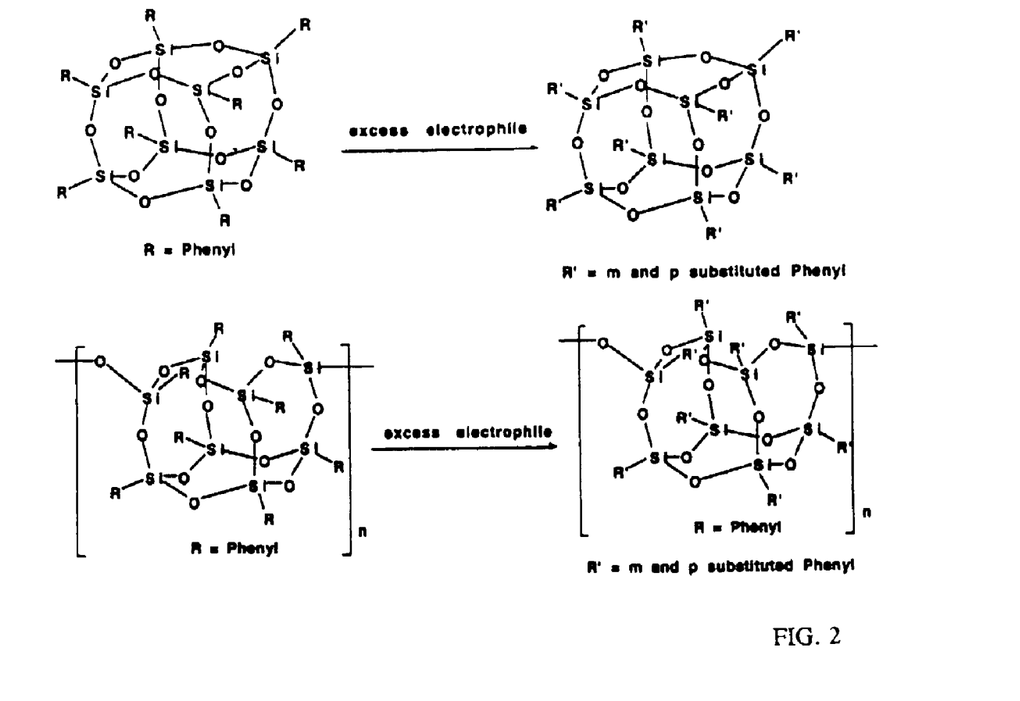
FIG. 2 illustrates preparation of "cube" and oligomeric "open cube" silsesquioxane cage-like structures where the silicon atoms are phenyl or substituted-phenyl substituted.
Figure 3:
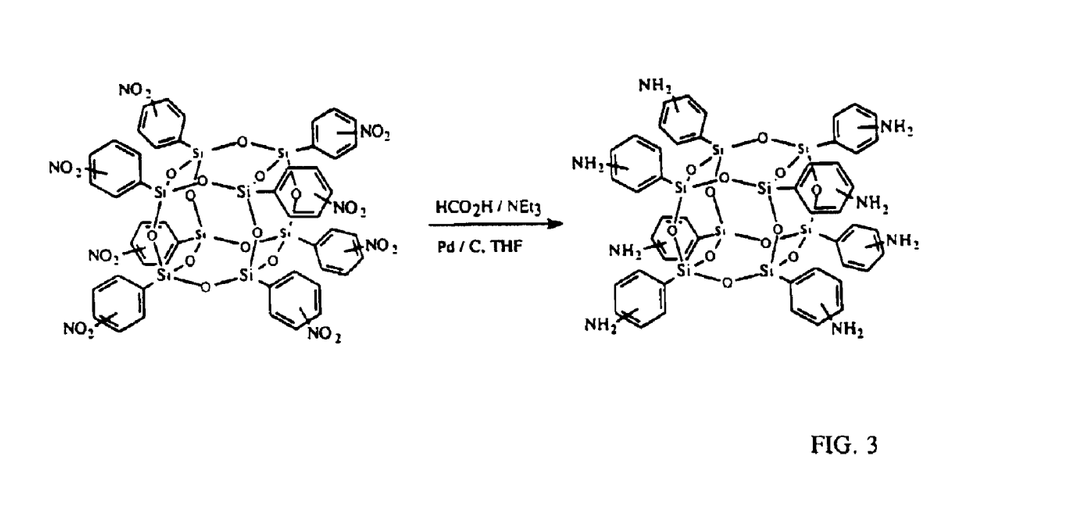
FIG. 3 illustrates the synthesis of aminofunctional-substituted silsesquioxanes from nitrophenyl-substituted silsesquioxanes.
Figure 4:
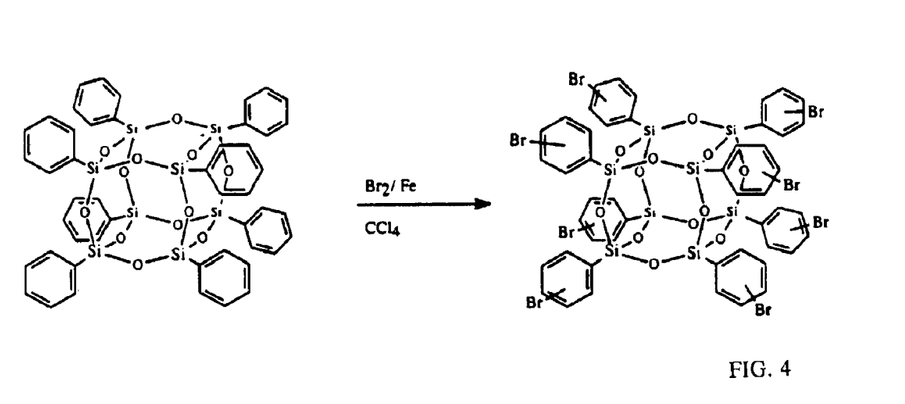
FIG. 4 illustrates a synthesis of an octakis(bromophenyl) silsesquioxane.
Figure 5:
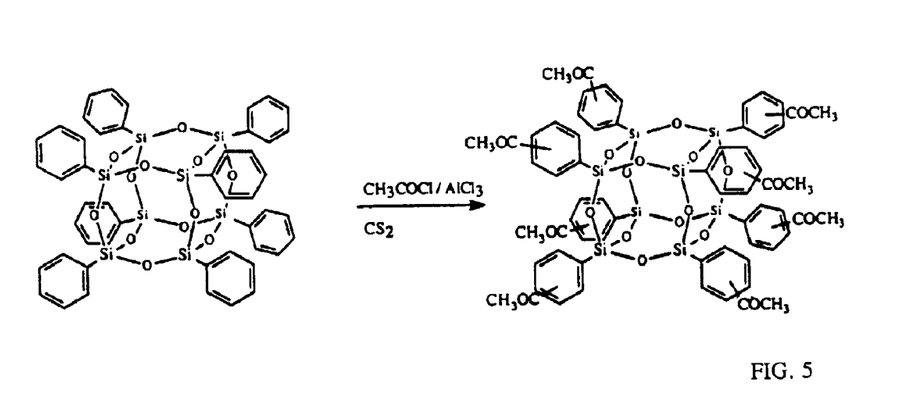
FIG. 5 illustrates a synthesis of an octakis(acetylphenyl) silsesquioxane.
Figure 6:
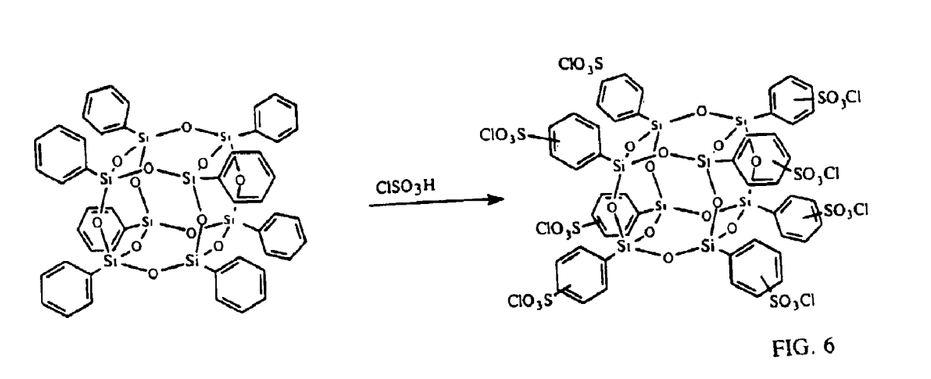
FIG. 6 illustrates a synthesis of an octakis (chlorosulfonylphenyl)silsesquioxane.
Figure 7:
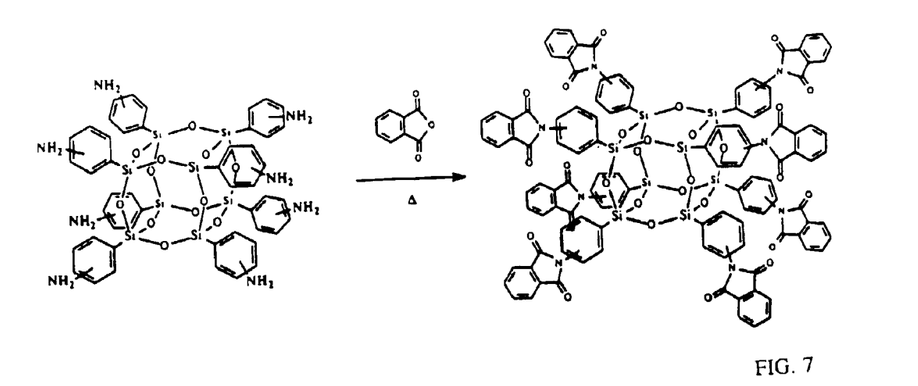
FIG. 7 illustrates a synthesis of an octakis (phthalimidophenyl)silsesquioxane.
Figure 8:
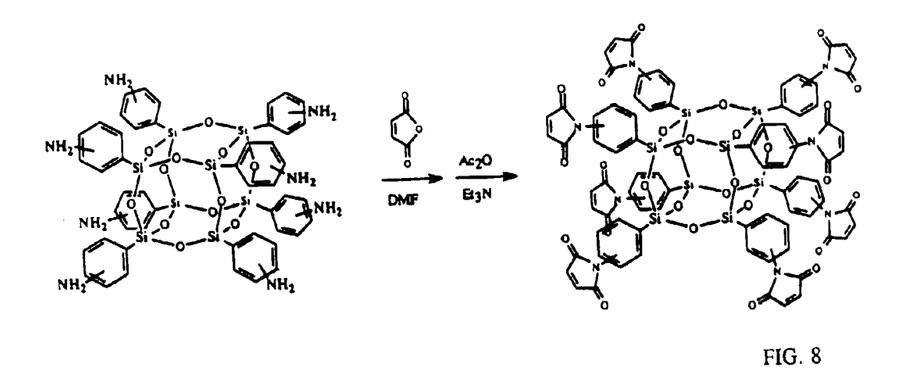
FIG. 8 illustrates a synthesis of an octakis (maleimidophenyl)silsesquioxane.

Most preferably, the silsesquioxane takes the form of a cage-like or ladder structure such as those illustrated in FIG. 1. Cage-like structures with from 8 to 16 silicon atoms are preferred. Most preferred are completely condensed cages having 8, 10, 12, or 16 silicon atoms or incompletely condensed cages having 7 or 8 silicon atoms. However, sheet-like structures are also possible. Moreover, larger structures which have a thickness of less than 100 nm and contain Si-bound functionalized phenyl groups are also within the scope of the invention.

The reactive, functionalized organic groups comprise an aryl group bearing reactive functionality. "Reactive" functionality is considered to be that type of functional group which can react to form a chemical bond with another molecule under conventional chemical reaction conditions without the use of "brute force." Common reaction conditions include those employed in hydrosilylation, condensation, addition, esterification, etherification, Michael reaction, imidation, amination, sulfonation, and the like. These reactions are those in common use to provide a wide variety of organic derivatives, oligomers, and polymers. Examples of reactive functionalities include epoxy, amino, hydroxy, (meth)acrylate, alkyl, maleimide, isocyanate, cyanate, carbonate, carbonylchloride, sulfonylchloride, silicon-bonded hydrogen ("Si—H"), and the like. The silsesquioxanes of the present invention which have a given functionality may be employed to produce silsesquioxanes with different functionality by suitable reaction. For example, a silsesquioxane where the phenyl groups are substituted with amino groups may be reacted with maleic anhydride to produce N-maleimidoaminophenyl ("maleimido" or "maleimide") functionality.

Silsesquioxanes bearing —$OSi(Me)_2H$ groups are known, as indicated previously. These compounds may be used to hydrosilylate a number of unsaturated compounds bearing functional groups, i.e. allylglycidylether, allylamine, isocyanatoethylmethacrylate, and the like. Such silsesquioxanes are highly useful as spacer molecules in the preparation of multilayer or core/shell ordered nanocomposites together with the functionalized phenyl silsesquioxanes of the present invention.

Preferably, the functional groups of the phenyl groups include reactive functional groups such as an amino, maleimido, isocyanato, or cyanato group. For the purposes of this invention, phenyl substituents such as alkoxy, nitro, alkyl, aryl, and the like are considered non-reactive.

The functionalized silsesquioxanes may be made from a variety of starting materials. When substituted phenyl-functionalized silsesquioxanes are contemplated, it is desirable, for example to employ phenyl silsesquioxanes such as octaphenylsilsesquioxane, commercially available by hydrolysis of phenyltrichlorosilanes as a starting material, or a phenyl-substituted silsesquioxane also containing less than about 50 mol % of alkyl groups, such as may be prepared by hydrolyzing a mixture of phenyltrichlorosilanes and methyltrichlorosilanes or (phenyldichloro)(methyldichloro)disiloxane. In such compounds, the alkyl substituent is virtually non-functionalizable, and will limit the overall functionality of the functionalized silsesquioxane. Preferably, the silsesquioxane is a perphenylsilsesquioxane, the phenyl groups of which serve as an admirable vehicle for functionalization by electrophilic substitution.

While numerous silsesquioxanes may be used as precursors to the O—$Si(Me)_2H$ functionalized silsesquioxanes of the prior art, the expense of the commonly used precursor is considerable. During the course of the investigations of the present invention, it was surprisingly discovered that inexpensive materials having high silica ("Q") content provide a source material for functionalized silsesquioxanes. Suitable source of silsesquioxane "skeleton" material, for example, are ash produced from silaceous sources, such as fly ash, rice hull ash, etc. Rice hull ash is a particularly preferred source material, since it is high in silica, and is available at very low cost. The preparation of O—$Si(R')_2H$ functionalized silsesquioxanes from such natural sources is also part of the present invention, where R' is a hydrocarbon or hydrocarbonoxy group. The products or derivatives may be used in conjunction with the functionalized phenyl silsesquioxanes of the present invention to provide useful products.

Rice hull ash, high in silica content, may be converted to an octaanion by reaction with tetraalkylammonium hydroxide. The octaanion salt may then be converted to the corresponding octakis[hydridomethylsiloxy] compound by reaction with chlorodimethylsilane. The reaction provides an octafunctional compound which contains an Si—H bonded hydrogen which can participate in hydrosilylation reactions to form a number of reactive derivatives. Such a synthetic route to functionalized silsesquioxanes has heretofore not been known. Most preferably, the synthesis takes place at 60–90° C. over approximately 1–4 days. The reaction time can be shortened to one day at reasonable yield if a reaction temperature of 80° C. is chosen, with reaction conditions of 1.4 mol rice hull ash (silica), 150 ml water, 110 ml methanol, and 300 ml of 20% tetramethylammonium hydroxide in methanol. Quaternary ammonium hydroxide is preferably used in at least stoichiometric amount, and may be used in as much as twice stoichiometric or more.

To functionalize phenyl silsesquioxanes, the phenyl groups may be nitrated, and the resulting nitrophenyl groups reduced by aminophenyl groups. The facile reduction of the nitrophenyl moieties is directly contrary to the inert character assigned to ONPS in the literature. These aminophenyl groups serve as a springboard to numerous phenylsilsesquisiloxanes substituted with reactive functional groups, or may themselves serve as reactive functionalized group-substituted silsesquioxanes. For example, the aminophenyl silsesquioxanes may be reacted with maleic anhydride to produce N-maleimidophenyl-functional silsesquioxanes, or with phosgene to produce chlorocarbonylamino groups Based on success with the nitration process, related approaches were used to generate other materials. Thus the octabromo analog was successfully prepared using very mild conditions, and polysulfonyl chloride and polyacetyl derivatives were also prepared. Note that Olsson et al make the point that polyarylsilsesquioxanes are not stable in sulfuric acid.

In the synthetic methods used, occasionally some phenyl groups are lost, leaving a material that can have one, two or rarely three Si—OH bonds. In addition, occasionally one Si corner is missing. This leads to novel incompletely condensed materials that are known in the literature for alkyl substituted silsequioxanes but not for phenyl and especially not for functionalized aromatic T-resins.

These examples are meant to be representative and one skilled in the art will recognize that related reactions such as the Gilch reaction, Friedel Craft alkylation and sulfonation reactions and many other aromatic functionalization procedures are possible despite the well-known propensity of arylsilane compounds to react at the silicon-aryl carbon bond, e.g. to undergo protodesilylation. In addition, other aromatic compounds including S and N heteroaromatics and polyaromatic silsesquioxanes should be amenable to similar modifications.

These functionalized materials offer access to a wide variety of novel macromonomers of use for diverse applications as well as for nanocomposites. For example, the OAPS and polyAPS can be used as: (1) substrates for peptide syntheses, (2) polymers for ion exchange resins, (3) surfactants for templating the formation of mesostructured materials, (4) precursors to 3-D polyaniline and polypyrrole conducting oligomers and polymers, (5) precursors for hole transport and emitting compounds for organic light emitting diodes (OLEDS), (6) for thin film organic transistors (TFOTs) and sensors, (7) for fire resistant materials, (8) for high temperature structural materials, (9) diazo dyes, etc. All or any of these functionalities may be incorporated in the nanostructured materials that can be constructured with the methods and materials developed in this patent application. Similar diverse applications are possible with the other functionalized aromatic silsesquioxanes made above.

For example, the octabromo materials can be employed in Heck or Suzuki reactions to make numerous materials for many of the same applications as for OAPS and polyAPS, e.g. OLEDS, TFOTs, sensors, as well as other areas. Materials made by coupling both compounds might serve as controlled porosity materials for photonic crystals or as traps for quantum dots, catalyst particles, etc. Those versed in the art will recognize the general utility of these materials.

Likewise the polysulfonyl compounds can be made into amido and sulfonic acid derivatives, used in Friedel crafts sulfonation reactions or because of the very high density of acid groups per unit volume they may serve as acid catalysts for numerous types of processing including chiral syntheses if coupled with other aromatics, as a proton transfer agent in proton conducting membranes, etc. Thus, there is every reason to use them for the fabrication of polyfunctional nanocomposites.

Figure 9:
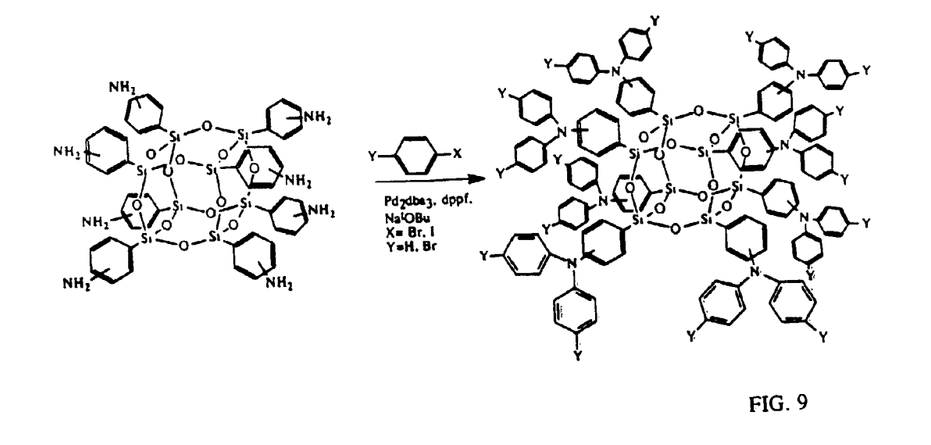
FIG. 9 illustrates replacement of amino hydrogens by phenyl or substituted phenyl groups which may be useful as hole carriers for organic light emitting diodes.
Figure 10:
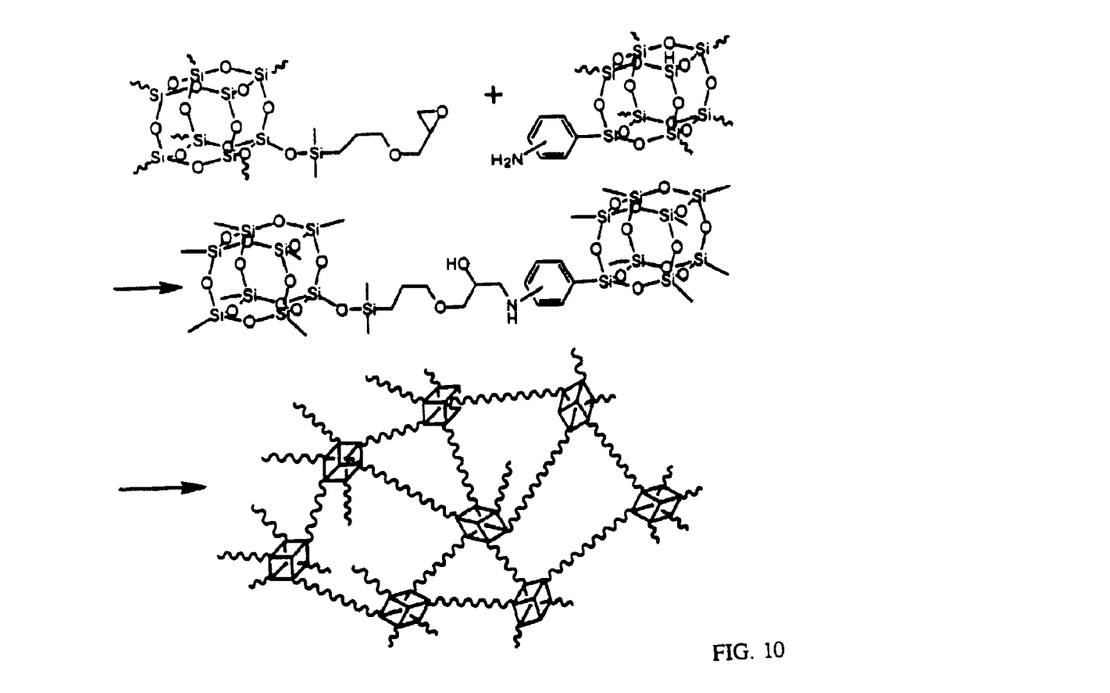
FIG. 10 illustrates schematically a nanocomposite prepared by reaction of an aminophenyl-substituted silsesquioxane with a glycidylpropyldimethylsiloxy-substituted silsesquioxane.
Figure 11:
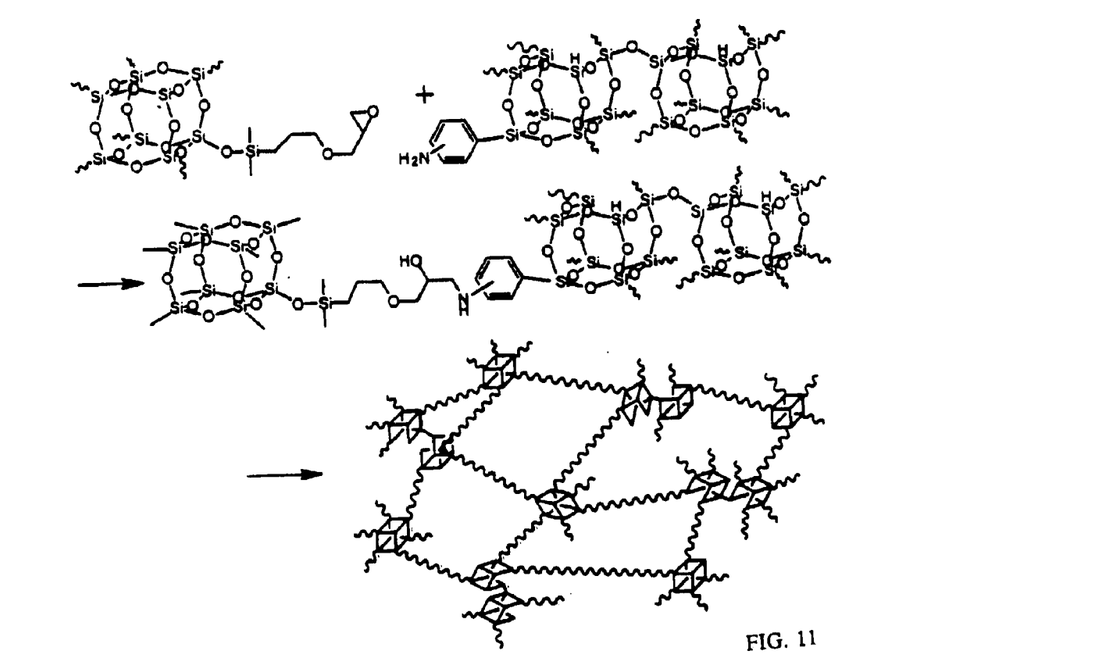
FIG. 11 illustrates schematically a nanocomposite prepared by reacting an aminophenyl-substituted silsesquioxane oligomer with a glycidylpropyldimethylsiloxy-substituted silsesquioxane.
Figure 12:
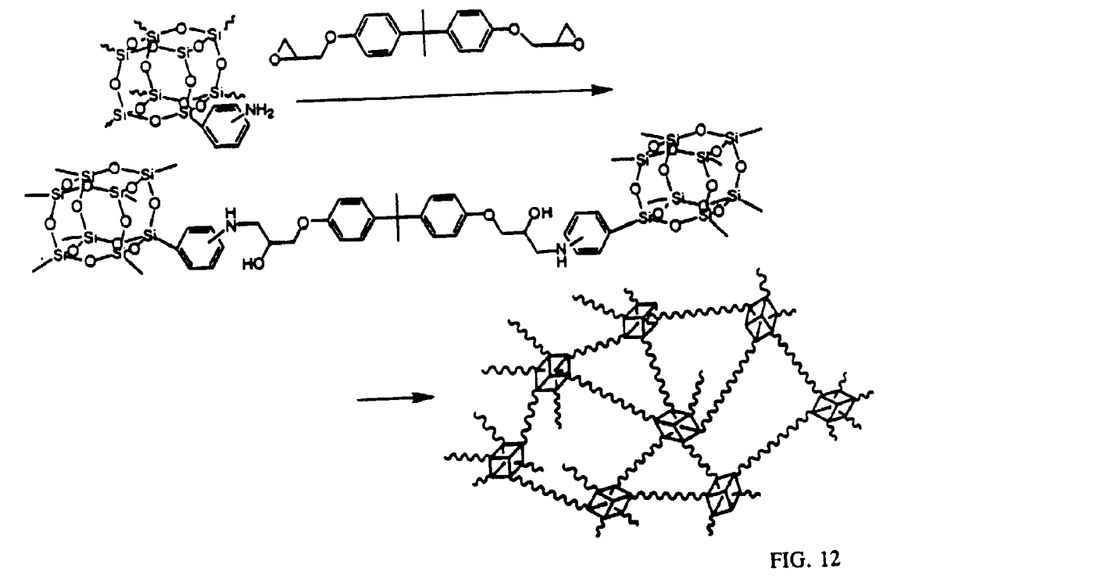
FIG. 12 illustrates schematically a nanocomposite prepared by coupling an aminophenyl-substituted silsesquioxane with a difunctional bisphenol A diglycidyl ether coupling agent.
Figure 13:
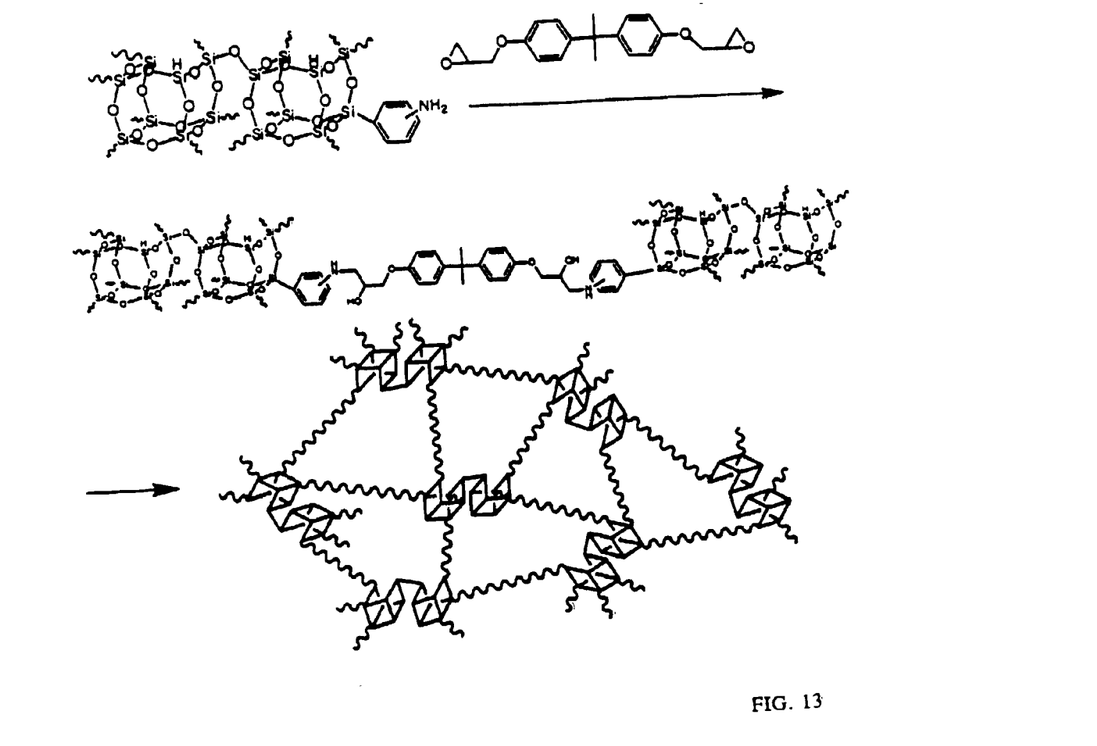
FIG. 13 illustrates schematically a nanocomposite prepared by coupling an aminophenyl-substituted silsesquioxane oligomer with a difunctional bisphenol A diglycidyl ether coupling agent.
Figure 14:
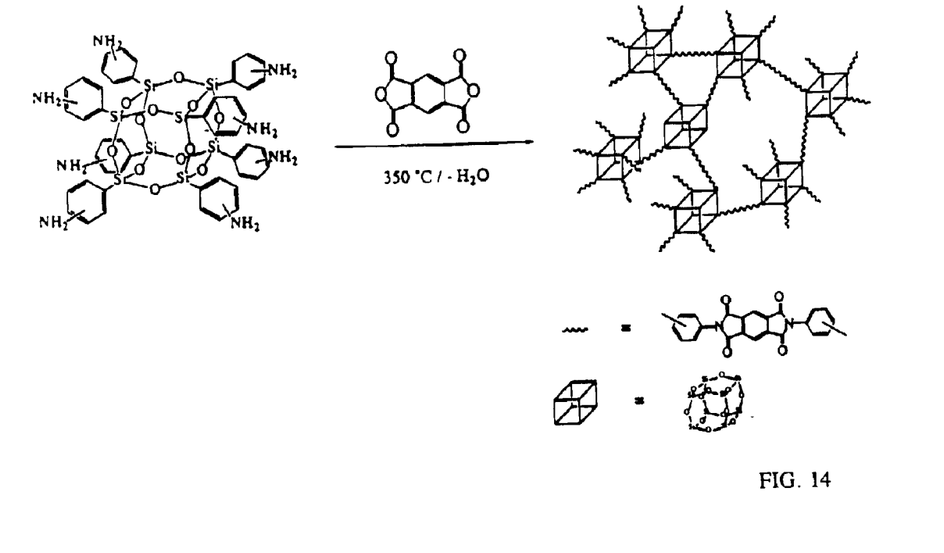
FIG. 14 illustrates schematically a nanocomposite having imide linkages between silsesquioxane "cubes" prepared by reacting an aminophenyl-substituted silsesquioxane with pyromellitic dianhydride.
Figure 15:
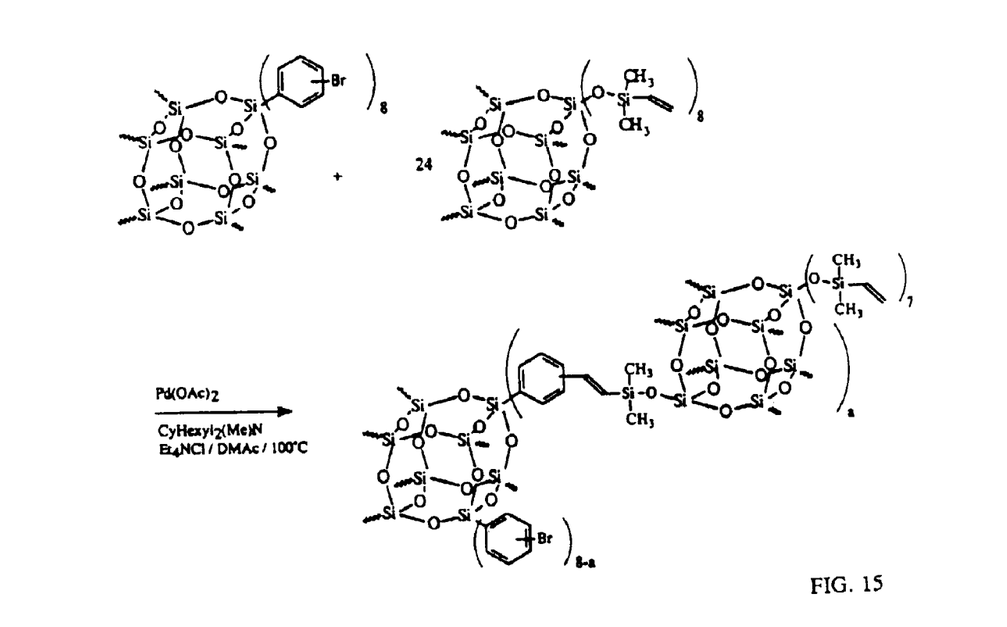
FIG. 15 illustrates schematically the preparation of a core/shell or layered multi-block nanocomposite structure by reaction of a first portion of functionalized phenyl silsesquioxane with a complementarily reactive second functionalized silsesquioxane.
Figure 16:
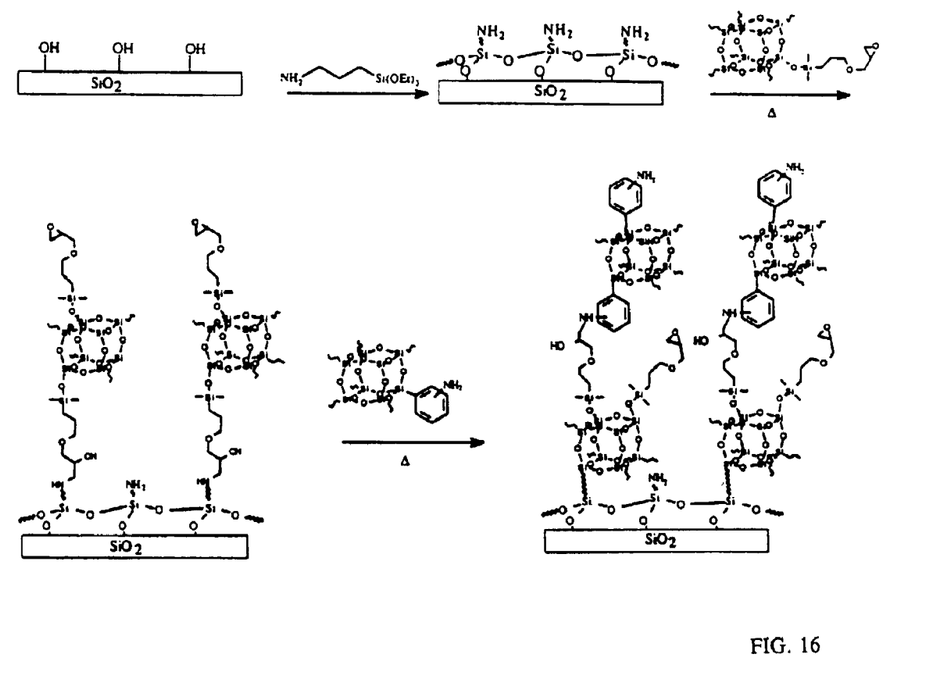
FIG. 16 illustrates the preparation of a multi-layer nanocomposite material on a substrate employing epoxy-functional silsesquioxanes and the aminophenyl-substituted silsesquioxanes of the present invention as complementarily reactive layer components.

FIG. 9 represents a model reaction demonstrating replacement of an amine hydrogen with a phenyl group as a potential model for making hole carriers for OLEDs or for making amides or even as a novel precursor or aryl/alkylammonium salts, etc.

It has been surprisingly discovered that the phenyl groups of phenylsilsesquioxanes are amenable to electrophilic substitution. It is possible, using such reactions, to substitute a wide variety of functional groups onto the phenyl groups. These groups, in turn, may be used to provide access to other functional groups which may not be useful in electrophilic substitutions. The degree of functionalization of the phenyl groups may be from 1 to 3 groups per phenyl ring, but the most useful number of functional groups is one per phenyl ring. Furthermore, the number of phenyl groups which are functionalized may range from one per silsesquioxane molecule, to being fully functionalized, i.e. one reactive functionality per each phenyl group. In general, it is preferable to functionalize 2 to 8 phenyl groups, more preferably 4 to 8 functional groups, when the silsesquioxanes are "cubes" having 8 silicon atoms. The total functionality may be tailored to the application. It should be noted that the term "precursor" means a functional group which is subsequently reacted or derivatized to form a desired functional group. For example, a nitro group may be a precursor to an amino group, and an amino group may be a precursor to an isocyanate group or a maleimido group.

Highly pure acetyloctaphenylsilsesquioxane ("AcOPS") can be produced in moderate yield via Friedel-Crafts acylation chemistry. Initial reactions in pure $CS_2$ resulted in high conversion, but were plagued by inconsistency due to solubility issues, as well as substantial Si—C cleavage. Reactions in nitrobenzene or mixed nitrobenzene/$CS_2$ systems provided more consistency and little or no cleavage, but limited (<70%) conversion and long reaction times. Reactions in mixed $CS_2/CH_2Cl_2$ provided fast, efficient reactions with little Si—C cleavage. The slightly high ceramic yield in the TGA trace is indicative of Si—C cleavage, and subsequent formation of Si—OH or bridged Si—O—Si dimers. The ceramic yield for the repeating unit HOSiO$_{1.5}$ is 87.0% and that of CH$_3$COC$_6$H$_4$SiO$_{1.5}$ is 35.1%. From these values, the fraction of cleaved groups is calculated to be 2.4%. This is consistent with the GPC data, which indicates 1.7% dimer, and the $^1$H-NMR spectra, which contains a trace Si—OH peak at 1.6 ppm. Lower reaction temperatures were found to improve yield and meta/para ratio.

Polyphenylsilsesquioxane can be acylated under the same optimized conditions for OPS in moderate yields. Conversion of phenyl to acetylphenyl is 90% (as per 1H-NMR). It is interesting to note that the polydispersity and molecular weight of the PPS decreases significantly upon acylation. This phenomenon was also observed upon nitration of PPS, and can be explained by the cleavage of Si—O—Si bridges and subsequent rearrangement during the acidic synthesis and work-up.

Nanocomposites have many uses. For example, many nanocomposite materials exhibit high heat deflection temperatures, i.e. nylon containing exfoliated clay particles; high gas barrier properties; high thermal stability; enhanced resistance to oxygen, as required for low earth orbit devices; controlled porosity; low k-dielectric materials; and use in constructing low-cost lasers and other electrooptical devices. A difficulty in many of such applications is establishing a controlled structure created from precisely defined nanostructural components. Nanosized fillers such as small particle size silica, exfoliated clay, and the like do not have the precisely controlled size required for designed nanocomposites, and in general lack useable functionality as well.

Without the ability to provide nanocomponents of specified structure and functionality, it is impossible to construct materials or devices which rely on predictable separation of nanocomponents, whether randomly distributed in a continuous matrix or reacted in successive layers with organic resins or other nanocomponent particles. Without predictable geometry at the nanocomponent level, the ability to predict non-linear pheomena, and therefore use in devices which rely on such non-linear behavior, is thwarted.

Many varieties of nanocomposite materials are made possible by the functionalized silsesquioxanes of the present invention. For example, simple filled polymers may be created by employing the functionalized phenyl silsesquioxanes ("FPSSO") of the present invention dispersed in a continuous thermoplastic or themoset matrix. Because of the extremely small size and the presence of significant reactive functionality, the FPSSO may be chemically bound to the matrix, generating a large proportion of interphase. Because the FPSSO are of predictable, repetitive size, composite properties may be absolutely uniform, a property not obtainable with fillers of random size and limited and often variable functionality.

The FPSSO may also be used to form layered structures. Such layered structures may be prepared by reacting a first layer of FPSSO, for example an octakis(aminophenyl) silsesquioxane ("OAPS") with a difunctional spacer molecule, for example a diisocyanate or diepoxide, followed by addition of a second layer of OAPS, etc., until a structure of the requisite number of layers is produced. Unreacted spacer molecules and OAPS may optionally be removed prior to creation of subsequent layers, if desired, by solvent washes. The OAPS may be first (or later) partially reacted with other components such as dyes, liquid crystalline reactive substances, chiral molecules, etc., to produce layers containing these components. Organic spacers which introduce further functionality, for example trifunctional, tetrafunctional, etc., spacers where the functionalities are the same or different, or organic spacers which provide novel physicochemical properties, i.e., electroluminescence, light absorption, etc, may also be used. The components in each layer may be the same or different.

Layered nanocomposites may also be prepared having successive layers of nanocomponents in the absence of spacer molecules by employing FSSO of complementary reactivity, or an FPSSO of the present invention and a glycidyl-functional silsesquioxane of the prior art, for example OAPS as a first FPSSO, and octakis(glycidyl) silsequioxane ("OG") as a complementary reactive nanostructure. When the nanocomponents are small, as in the present invention, for example having an overall size of less than 5 nm, the resulting materials will resemble purely interphase material rather than bulk material, and significant alteration of macroscopic properties will result. Such products are novel.

To illustrate the possibilities possible with the present invention FPSSO, a series of nanocomposite structures were prepared employing amine cured epoxy resins. The amine curing agent was standard 4,4'-diaminodiphenylmethane ("DDM"). As epoxy components were used a standard bisphenol A epoxy resin (DGEBA) having a molecular weight of about 340, and OG and octakis (ethylcyclohexylepoxy)silsesquioxane ("OC") as FSSO. Tensile and fracture toughness of test specimens were measured. The test specimens were made at various "N" ratios of NH$_2$:epoxy, followed by curing at 150° C. for 10 hours in nitrogen atmosphere. It was found that the thermal stability of both the OC/DDM and OG/DDM polymers was considerably higher than that of DGEBA/DDM. For example, a 5% weight loss was noted by TGA for the DGEBA/DDM polymer at 340° C., while the OC/DDM nanocomposite polymer experienced the same loss at 410° C., some 70° C. more stable. The storage modulus curves of both the OC/DDM and DGEBA/DDM materials were similar in shape at all NH$_2$:epoxy group ratios. Surprisingly, however, at an NH2/epoxy ratio of 0.5, the OG/DDM nanocomposite material exhibited only a slow decline in storage modulus with increasing temperature, with no observable Tg. At an NH$_2$/epoxy ratio of 1.25, an OC/OG/DDM nanocomposite material (OC/OG=20/80 by mol) gave elastic moduli comparable with the best DGEBA/DDM moduli; and a fracture toughness which was exceptionally high for an epoxy resin.

In addition to the aforementioned physicochemical properties available from FPSSO, the nanocomponents of the present invention offer other advantages as well: they are easily purified; they offer high Tg with little tendency to crystalize, but do form liquid crystals; they are easily processed by spray, spin, and dip coating, or by casting, both from solution and from the melt; they are extremely resistant to thermal, oxidative, or hydrolytic degradation; and they provide an extremely high density of varied or identical functionality in a small volume.

Building Block Materials:

EXAMPLE 1

Synthesis of Octa(nitrophenyl)silsesquioxane (ONPS)

To 30 ml of fuming nitric acid was added with stirring and cooling in ice water 5.0 g (4.8 mmol) of OPS in small portion. After all has been added, the solution was stirred at 0° C. for 30 min and further stirred at room temperature for another 20 h. The solution was then poured on 250 g of ice. When the ice has melted, a very faintly yellow precipitate was collected, washed with water and then with acetonitrile.

The obtained powder was dried in a vacuum oven to remove residual solvent (70° C. for 4 h). Weight 3.0 g (2.2 mmol, recovery 46%). Chemical analysis, thermal and spectral data are listed below.

| Octanitrophenylsilsesquioxane | |
|---|---|
| $^1$H-NMR (acetone-d6) | 8.7 (t, 1.0H), 8.4-8.0 (m, 4.1H), 7.8 (m, 2.7H) |
| $^{13}$C-NMR (acetone-d6) | 154.0, 148.9, 141.0, 138.6, 136.5, 135.3, 134.1, 132.3, 130.8, 129.5, 127.0, 125.2, 123.6 |
| $^{29}$Si-NMR (THF, TMS, acetone-d6, ppm) | −79.2, −83.0 |
| FT-IR (cm$^{-1}$) | 3090 (δC—H), 1533, 1350 (δN=O), 1138 (δSi—O) |
| TGA (air/wt %/1000° C.) | 33.7 (cal. 34.5) |
| TGA (N$_2$/wt % 1000° C.) | — |
| Elemental Analysis | % C: 41.3 (41.4)  % H: 2.4 (2.3) % N: 8.0 (8.0) |
| GPC | Mn = 1057, Mw = 113, Mw/Mn = 1.07 |

| Octaphenylsilsesquioxane (for comparison) | |
|---|---|
| $^1$H-NMR (CDCl$_3$, ppm) | 7.44 (dd, 2.0H), 7.42 (t, 0.84H), 7.34 (t, 1.9H) |
| $^{13}$C-NMR (CDCl$_3$, ppm) | 139.4, 134.2, 130.8, 127.9 |
| $^{29}$Si-NMR (CDCl$_3$, ppm) | 3050 (δC—H), 1596, 1496 (δC=C), 1138 (δSi—O) |
| TGA (air/wt %/1000° C.) | 9.1 (cal. 45.6%) |
| TGA (N$_2$/wt %/1000° C.) | 0 |
| Elemental Analysis (%) | NA |
| GPC | Mn = 707, Mw = 711, Mw/Mn = 1.01 |

Example 2

Synthesis of Octa(acetylphenyl)silsesquioxane (OAcPS)

Into a 50 ml of schlenk flask was placed 0.522 g (3.92 mmol) of aluminum chloride with 5 ml of CS$_2$. The mixture was stirred at 0° C. under nitrogen for 15 min. OPS (0.5 g, 0.484 mmol, -Ph 3.87 mmol) was then added to the mixture with stirring and the suspension was stirred at 0° C. for 30 min and 20 h at room temperature. To quench the reaction, 5 g of ice was added and the organic layer was extracted with 10 ml of methylene chloride. The organic layer was washed with water until the aqueous layer became pH=~7 and dried over sodium sulfate. Undissolved powder was removed from the methylene chloride solution by filtration and the obtained clear solution was added dropwise into 50 ml of hexane, which gave white powder. The powder was collected by filtration and washed with hexane. Yield was 0.319 g (60.1%) (assuming the conversion of the phenyl group to the acetylphenyl group was 66.9%. Analytical data are in Table 1.

| Octaacetylphenylsilsesquioxane | |
|---|---|
| $^1$H-NMR (CDCl$_3$) | 8.3 (m, 0.86H), 7.9 (m, 1.7H), 7.7 (m, 1.0H), 7.5-7.0 (m, 2.9H), 2.5 (m, 3.0H) |
| $^{13}$C-NMR (CDCl$_3$) | 198.1, 138.6, 136.3, 134.1, 131.1, 129.7, 128.5, 26.4 |
| $^{29}$JSi-NMR (THF, TMS, acetone-d6, ppm) | — |
| FT-IR (cm$^{-1}$) | 3390 (broad, δO—H), 3061 j(δC—H), 1690 (δC=O), 1596, 1432, 1362 (δC=C) 1138 (δSi—O) |
| TGA (air/wt %/1000° C.) | 38.4 (cal. 38.9, assumes 66.9% conversion of Ph to acetyl Ph) |
| TGA (N$_2$/wt %/1000° C.) | — |
| Elemental Analysis | % C: 47.1 (56.0) assumes 66.9%) % H: 3.7 (4.1) |
| GPC | Mn = 990, Mw = 1089, Mw/Mn = 1.10 |

Example 3

Synthesis of Octa(acetylphenyl)silsesquioxane (OAcPS)

The same reaction conditions as in Example 2 were used except the reaction temperature. After mixing all the reagents, the mixture was refluxed under nitrogen for 1 h and ethyl acetate was used for the extraction instead of methylene chloride. Yield was 0.44 g (76%). Analytical data are in Table 1.

| Octaacetylphenylsilsesquioxane | |
|---|---|
| $^1$H-NMR (CDCl$_3$) | 8.3 (m, 1.0H), 8.0 (m, 1.9H), 7.5 (m, 1.1H), 2.5 (m, 3.0H) |
| $^{13}$C-NMR (CDCl$_3$) | 198.2, 138.6, 136.6, 134.0, 131.1, 129.7, 128.5, 26.5 |
| $^{29}$Si-NMR (THF, TMS, acetone-db, ppm) | −80.0 |
| FT-IR (cm$^{-1}$) | 3320 (broad, δO—H), 3060 (δC—H), 1690 (δC=O), 1593, 1417, 1360 (δC=C), 1139 (δSi—O) |
| TGA (air/wt %/1000° C.) | 42.3 (cal. 35.1) |
| TGA (N$_2$/wt %/1000° C.) | — |
| Elemental Analysis | % C: 49.4 (56.1)  % H: 4.0 (4.1)  % N: — |
| GPC | Mn = 1006, Mw = 1060, Mw/Mn = 1.05 |

Example 4a

Synthesis of Octa(bromophenyl)silsesquioxane (OBrPS)

Into a 20 ml of schlenk flask equipped with a condenser was placed OPS (0.5 g, 0.484 mmol, -Ph, 3.87 mmol) followed by addition of 5 ml of carbon tetrachloride and Fe (0.0324 g, 0.580 mmol). While the mixture was refluxed under nitrogen, bromine (0.106 ml, 2.06 mmol) was slowly added and the mixture was refluxed for 1 h. Then Fe (0.0324 g, 0.580 mmol) and bromine (0.106 ml, 2.06 mmol) was added and refluxed. After 1 h, Fe (0.0324 g, 0.580 mmol) and bromine (0.106 ml, 2.06 mmol) was added again and refluxed another 1 h. Fe (0.0108 g, 0.144 mmol) was added and the mixture was heated for another 1 h. The mixture was washed twice with 10 ml of water with 1.0 ml of saturated NaHSO$_3$ after addition of 30 ml of ethylacetate. The organic layer was washed with brine and dried over Na$_2$SO$_4$ then condensed to 5 ml under reduced pressure. The white powder was obtained by reprecipitation into 100 ml of cold methanol and the following filtration. Yield 0.54 g (0.324 mmol, 66.9%). Analytical data are in Table 1.

| Octabromophenylsilsesquioxane | |
|---|---|
| $^1$H-NMR (CDCl$_3$) | 8.1-7.5 (m, 1.7H), 7.45 (s, 1.0H), 7.3 (m, 0.47H) |
| $^{13}$C-NMR (CDCl$_3$) | 140.5, 137.1, 135.8, 134.5, 133.8, 132.9, 132.5, 131.4, 129.9, 127.2, 126.5, 122.9, 121.3 |

-continued

| Octabromophenylsilsesquioxane | |
|---|---|
| $^{29}$Si-NMR (THF, TMS, acetone-d6, ppm) | −78.9, −80.4, −82.1, −83.5 |
| FT-IR (cm$^{-1}$) | 3070 (δC—H), 1580, 1446, 1357 (δC=C), 1143 (δSi=O) |
| TGA (air/wt %/1000° C.) | 22.5 (cal. 28.9) |
| TGA (N$_2$/wt %/1000° C.) | — |
| Elemental Analysis | % C: 27.3 (34.6)   % H: 1.3 (1.9) |
| GPC | Mn = 846, Mw = 852, Mw/Mn = 1.01 |

Example 4b
Synthesis of Octa(bromophenyl)silsesquioxane (OBrPS)

Into 25 ml of schlenk flask equipped with a condenser was placed OPS (0.5 g, 0.484 mmol), -Ph 3.87 mmol) followed by addition of 5 ml of carbon tetrachloride. While the mixture was refluxed under nitrogen, bromine (0.106 ml, 2.06 mmol) was slowly added using a glass pipet and the mixture was refluxed for 1 h. The procedure was repeated three times. The mixture was washed twice with 10 ml of water with 1.0 ml of saturated NaHSO$_3$ after addition of 30 ml of ethylacetate. The organic layer was washed with brine and dried over Na$_2$SO$_4$ then condensed to 5 ml under reduced pressure. The white powder was obtained by reprecipitation into 100 ml of cold methanol and the following filtration. Yield 0.418 g (0.404 mmol, 83.5%). Analytical data are in Table 1.

| Octabromophenylsilsesquioxane (recovered OPS only) | |
|---|---|
| $^1$H-NMR (CDCl$_3$) | 7.44 (m, 1.0H), 7.62 (m, 0.34H), 7.42-7.28 (m, 1.9H) |
| $^{13}$C-NMR (CDCl$_3$) | 139.8, 134.2, 130.8, 127.9 |
| $^{29}$Si-NMR (THF, TMS, acetone-d6, ppm) | — |
| FT-IR (cm$^{-1}$) | — |
| TGA (air/wt %/1000° C.) | — |
| TGA (N$_2$/wt %/1000° C.) | — |
| GPC | Mn = 703, Mw = 706, Mw/Mn = 1.01 |

Example 5
Synthesis of Octa(aminophenyl)silsesquioxane (OAPS) Without Fe Into a 100 ml schlenk flask equipped with a condenser were placed ONPHS (2.0 g, 1.435 mmol, —NO$_2$ 11.48 mmol) and 5 wt % Pd/C (244 mg, 0.115 mmol). Distilled THF (20 ml) and triethylamine (16.0 ml, 114.8 mmol) were added to the mixture under nitrogen. The mixture was heated to 60° C. and 85% formic acid (2.09 ml, 46.0 mmol) was added slowly at 60° C. under nitrogen with vigorous stirring with a magnetic stir bar. Carbon dioxide evolved with the addition of formic acid and the solution separated into two layers. After 5 h stirring, the THF layer was separated by decantation. 40 ml of THF was added to the black slurry and the solution separated previously were mixed and filtered through a funnel equipped with a glass filter and celite filter reagent to remove the catalyst. The volume of the solution was then reduced to 20 ml under reduced pressure and was put in a separatory funnel with 30 ml of water and 30 ml of ethyl acetate. The solution was washed 5× with 150 ml aliquots of water to remove triethylammonium formate and then washed with saturated aq. NaCl (30 ml). The organic layer was then dried over 1 g of Na$_2$SO$_4$ and added dropwise to 300 ml of hexane. A slightly brown powder precipitated which was collected by filtration. The powder was then dissolved in 20 ml of THF and reprecipitated into 200 ml of hexane to remove remaining triethylamine. The obtained powder was dried under vacuum. Yield 1.36 g (1.18 mmol, recovery 82.1%). Chemical analysis, thermal and spectral data are listed in Table 1.

| Octa(aminophenyl)silsesquioxane | |
|---|---|
| $^1$H-NMR (acetone-d6) | 7.8-6.2 (m, 4.0H), 5.2-3.7 (m, 2.0H), |
| $^{13}$C-NMR (acetone-d6) | 154.0, 148.1, 136.6, 132.8, 129.3, 123.4, 120.8, 117.3, 115.8, 114.4 |
| $^{29}$Si-NMR (THF, TMS, acetone-d6, ppm) | −73.3, −77.4 |
| FT-IR (cm$^{-1}$) | 3380 (broad, δN—H), 3050 (δC—H, 1623, 1597, 1485, 1441 (δC=C), 1130 (δSi=O) |
| TGA (air/wt %/1000° C.) | 41.1 (cal. 41.7) |
| TGA (N$_2$/wt %/1000° C.) | 60.0 |
| Elemental Analysis | % C: 48.4 (45.0)   % H: 4.2 (4.2) % N: 9.5 (9.7) |
| GPC | Mn = 1057, Mw = 1133, Mw/Mn = 1.07 |

Example 6
Synthesis of Octa(propylglycidyletherdimethylsiloxy)silsesquioxane (OG)

0.01 mol of octahydrido spacer cube is added to a 1 L round bottom three neck flask equipped with a stirring bar and a condenser. The flask is evacuated and refilled with nitrogen three times and heated to 90° C. Distilled toluene is added until all the powder is dissolved to give a clear solution. Allyl glydicyl ether in excess is then added to the flask followed by a catalytic amount of a 2.0 mM solution of dicylcopentadienyl platinum [Pt(dcp)]. Care is taken to release the pressure from the flask while the initial reaction is occurring; the heat generated from the reaction increases the local temperature and the solvent evaporates, building up the pressure.

Example 7
Synthesis of Octa(sulfonylchlorophenyl)silsesquioxanes (OSCIPS)

To a 25 ml schlenk flask was added chlorosulfonic acid (5.0 ml). The flask was then cooled to 0° C. and OPS (0.5 g, 0.484 mmol, Ph 3.87 mmol) was added slowly under nitrogen flow. The mixture was stirred at 0° C. for 2 h under nitrogen and added into ice water (10 ml). The product was extracted with 10 ml of ethyl acetate and dried over sodium sulfate. After condensing the volume to 5 ml under pressure, the solution was precipitated into hexane (50 ml) and collected by filtration and dried under vacuum over night. Yield was 0.147 g (conversion to sulfonylchlorophenyl group was calculated to be 62% based on TGA measurement in air. From this conversion degree, the yield was recalculated to be 45%).

| Octa(sulfonylchlorophenyl)silsesquioxanes (0° C. 2 h) | |
|---|---|
| $^1$H-NMR (acetone-d6) | 8.6-7.0 (broad peak), 8.10 (m), 7.92 (m), 7.60 (m) |
| $^{13}$C-NMR (acetone-d6) | 145.0, 142.1, 136.7, 134.9, 132.5, 131.1, 130.4, 128.4, 127.7 |
| $^{29}$Si-NMR (THF, TMS, acetone-d6, ppm) | — |
| FT-IR (cm$^{-1}$) | 3600 (broad, vO—H), 1382 (vS=O), 1185 (δSi—O) |

-continued

| Octa(sulfonylchlorophenyl)silsesquioxanes (0° C. 2 h) | |
|---|---|
| TGA (air/wt %/1000° C.) | 34.0 (cal. 26.4) |
| TGA (N₂/wt %/1000° C.) | — |
| Elemental Analysis | % C: 31.8 (31.7)  % H: 2.4 (1.8) |
| GPC | Mn = 1186, Mw = 1270, Mw/Mn = 1.07 |

Example 8
Synthesis of Polynitrophenylsilsesquioxanes (PHPhS)

To a 250 ml flask was added 33 ml of fuming nitric acid (90 wt %). Polyphenylsilsesquioxane (Gelest, Inc., product number SST-3p01) (PPhS, 5.5 g, 42.6 mmol) was then added slowly at 0° C. in air and the mixture was stirred at room temperature for 4 h. The solution was filtered through a glass filter and added dropwise into ice. The obtained slightly brown powder was washed with water until the filtrate became neutral and was air dried. The powder was further washed with ethanol and dried in vacuum. The yield was (5.85 g).

Synthesis of Nanocomposite Materials

Example 9
Synthesis of N-phenylOAPS

Tris(dibenzylideneacetone)dipalladium (0) 95.2 mg, 0.104 mmol) and 2-(diphenylphosphino)ferrocene (84.6 mg, 0.153 mmol) were placed in a 100 ml flask equipped with a condenser and dissolved in 40 ml of dry toluene. The mixture was stirred 15 min at room temperature under nitrogen. Bromobenzene (0.730 mo, 6.93 mmol) was added to the mixture and stirred at room temperature under nitrogen another 15 min. To the mixture, OAPhS (0.50 g, 0.434 mmol, N:3.47 mmol) and NaOtBu (0.666 g, 6.94 mmol) were added. The mixture was heated at 80° C. for 3 h. After cooling to room temperature, the mixture was filtered to remove undissolved salt and washed with 80 ml of buffer solution. The organic layer was dried over $Na_2SO_4$ and mixed with 2 g of activated charcoal. After removal of charcoal, the toluene solution was added into 200 ml of hexane. The brown powder was collected by a filtration and dried under vacuum. Yield 0.371 g, 38.1%. (Yield was calculated assuming complete substitution).

| N-phenyl OAPS | |
|---|---|
| ¹H-NMR (CDCl₃) | 8.0-6.0 (m, 4H), 5.0-5.0 (broad singlet, 0.24H), 4.5-3.5 (broad singlet, 0.4H), 1.4-0.6 (broad singlet, 0.76H) |
| ¹³C-NMR (CDCl₃) | 142.7, 136.0, 131.8, 129.2, 126.6, 124.2, 120.8, 117.7 |
| ²⁹Si-NMR (THF, TMS, acetone-d6, ppm) | — |
| FT-IR (cm⁻¹) | 3400 (broad, vN—H), 3060, 2980 (vC—H), 1514, 1496, 1398 and 1368 (δC═C), 1130 (δSi—O) |
| TGA (air/wt %/1000° C.) | — |
| TGA (N₂/wt %/1000° C.) | — |
| Elemental Analysis | % C: —  % H: —  % N: — |
| GPC | Mn = 1186, Mw = 1270, Mw/Mn = 1.07 |

Example 10
Synthesis of Octa(phthalimidephenyl)silsesquioxane (OPIPS)

To a 25 ml schlenk flask equipped with a condenser were placed OAPS (0.5 g, 0.433 mmol) and phthalic anhydride (1.642 g, 11.1 mmol). The mixture was heated under nitrogen at 180° C. for 2 h. At this temperature, the anhydride melted and the mixture formed a homogeneous brown solution. After cooling down to room temperature, the mixture was dissolved in 20 ml of dichloromethane and filtered. After removing the solvent under reduced pressure, the remaining phthalic anhydride was removed by sublimation (0.6 mmHg, 130° C.). Yield 0.702 g (0.320 mmol, recovery 73.9%).

| Octa(phthalimidephenyl)silsesquioxane | |
|---|---|
| ¹H-NMR (CDCl₃) | 8.2-6.4 (broad peak) |
| ¹³C-NMR (CDCl₃) | 166.8, 137.0, 134.8, 131.5, 128.4, 123.3 |
| ²⁹Si-NMR (THF, TMS, acetone-d6, ppm) | — |
| FT-IR (cm⁻¹) | 3060 (δC—H), 1787, 1722 (δC═O), 1377 (δC—N), 1115 (δSi—O) |
| TGA (air/wt %/1000° C.) | 20.0 (21.9) |
| TGA (N₂/wt %/1000° C.) | — |
| Elemental Analysis | %C: —  % H: —  % N: — |
| GPC | Mn = 1673, Mw = 1931, Mw/Mn = 1.16 |

Example 11
Synthesis of Octa(maleimidophenyl)silsesquioxane (OMPIS)

To a 25 ml schlenk flask equipped with a condenser was placed maleic anhydride (0.340 g, 3.46 mmol) in 2.5 ml of DMF, and OAPS (0.5 g, 0.433 mmol) in 5.0 ml of DMF, was added under nitrogen at room temperature. The mixture was stirred at room temperature for 1 h under nitrogen. To the mixture, acetic anhydride (0.820 ml, 8.68 mmol) and triethylamine (0.071 ml, 0.868 mmol) were added. The mixture was then heated at 60° C. for 3 h under nitrogen. After cooling down to room temperature, the mixture was mixed with ethyl acetate (10 ml) and washed with water until the aqueous layer became neutral. The separated organic layer was dried over sodium sulfate (~1 g) and reprecipitated into hexane (100 ml). The powder was collected by filtration and dried under vacuum. Yield 0.616 g (0.343 mmol, 79.1%).

| Octa(maleimidephenyl)silsesquioxane | |
|---|---|
| ¹H-NMR (CDCl₃) | 8.2-6.8 (broad peak, 7H), 7.0 (s, 2H) |
| ¹³C-NMR (CDCl₃) | 170.4, 165.6, 144.0, 135.3, 134.0, 132.6, 129.7, 126.7, 124.0 |
| ²⁹Si-NMR (THF, TMS, acetone-d6, ppm) | −71.0, −79.3 |
| FT-IR (cm⁻¹) | 3082, 2934 (δC—H), 1800, 1719 (δC═O), 1581, 1554, 1484, 1425 (δC═C), 1380 (δC—N), 1136 (δS—O) |
| TGA (air/wt %/1000° C.) | 25.0 (26.8) |
| TGA (N₂/wt %/1000° C.) | — |
| Elemental Analysis | % C: —  % H: —  % N: — |
| GPC | Mn = 1648, Mw = 2042, Mw/Mn = 1.24 |

Example 12
Synthesis of Epoxide Nanocomposite from OAPS and OG

In formulating OAPS/OG composites, various molar ratios of $NH_2$ (in OAPS) to epoxy groups (in OG) ("N") were employed, i.e. N=0.3, 0.5, 0.75, and 1. The procedure used is as follows:

OAPS powder was weighed into a 20 ml glass vial containing a magnetic stirring bar. THF (2 ml) was added to the vial and the OAPS dissolved completely on stirring. OG was then added to the solution and the mixture was stirred vigorously to give a homogeneous solution. The dark yellow solution was then transferred into the aluminum mold (30 mm×13 mm×30 mm) and THF was slowly evaporated under vacuum at room temperature. The mixture was cured for 24 h at room temperature under $N_2$, followed by 6 h at 80° C. and then 6 h at 150° C. The final sample was 30 mm×13 mm×3 mm in size. Rough sample edges were removed by polishing with SiC paper prior to DMA testing.

Example 13
Synthesis of Epoxide Nanocomposite from PolyAPS and OG

In formulating PolyAPS/OG composites, a variable Phr was defined as parts of amine per hundred of epoxy resin by weight (a variable N was not used because the exact structure of PolyAPS was not known and thus the exact ratio of $NH_2$:epoxy ring could not calculated). The Phr is the conventional variable in industry for the formulation of general epoxy resins and amines. Compositions with phr values of 20, 35, 50, and 65 were prepared. PolyAPS/OG composites were prepared following the same method as in Example 11. The mixture of PolyAPS/OG in THF was a brown color compared with the yellow of OAPS/OG solution. The curing procedure for PolyAPS/OG was also the same as in Example 11. The final sample was 30 mm×13 mm×3 mm in size. Rough sample edges were removed by polishing with SiC paper prior to DMA testing.

Example 14
Synthesis of Epoxide Nanocomposite from OAPS and DGEBA

As in Example 11, a variable N was used for the formulation of OAPS/DGEBA composites, at N=0.3, 0.5, 0.75, and 1. OAPS powder was weighted into a 20 ml glass vial containing a magnetic stirring bar. THF (2 mL) was added to the vial and the OAPS dissolved completely on stirring. DGEBA was then added to the solution and the mixture was stirred vigorously to give a homogeneous solution. The dark yellow, transparent solution was then transferred into the aluminum mold (30 mm×13 mm×30 mm) preheated at 50° C. THF was slowly removed under vacuum at this temperature. The mixture was cured for 12 h at 50° C., then 6 h at 100° C. and finally 6 h at 150° C. under nitrogen. The final sample was 30 mm×13 mm×3 mm in size. Rough sample edges were removed by polishing with SiC paper prior to DMA testing.

Example 15
Synthesis of Epoxide Nanocomposite from PolyAPS and DGEBA

As in Example 12, a variable Phr was used for the formulation of PolyAPS/DGEBA, Phr=20, 35, 50 and 65. PolyAPS/DGEBA composites were prepared following the same method as in Example 12. The mixture of PolyAPS/DGEBA in THF was a brown color compared with the yellow of the OAPS/OG solution. Curing procedure for PolyAPS/DGEBA was also the same as in Example 12. The final sample was 30 mm×13 mm×3 mm in size. Rough sample edges were removed by polishing with SiC paper prior to DMA testing.

Example 16
Synthesis of Polyimide Nanocomposite from OAPS and Pyromellitic Dianhydride (PMDA)

To a 1-methyl-2-pyrrolidone (NMP 1.9 ml) solution of OAPhS (0.1 g) was added an NMP (1.4 ml) solution of PMDA at 0° C. under nitrogen. The mixture was stirred 3 min at the same temperature and added into an aluminum container. The mixture gelled immediately. The gel (amic acid gel) was then cured in a quartz tube under nitrogen at 130° C. for 2 h and 350° C. for 4 h. The ramp rate was 5° C./min. The solid obtained was further dried at 150° C. in vacuum for 2 h and was subjected to further analysis.

| Spectroscopic data. Polyimide Nanocomposite from OAPS and Pyromellitic Dianhydride (PMDA): (Curing temperature 350° C.) | |
|---|---|
| FT-IR ($Cm^{-1}$) | 3071 ($\delta$C—H), 1780, 1726($\delta$C=O), 1367 ($\delta$C—N), 1120 ($\delta$Si—O), |
| TGA (Air/wt %/1000° C.) | 25.9 (25.5) |
| TGA ($N_2$/wt % 1000° C.) | 75.6 |

| Thermal Properties of OAPS/PMDA Nanocomposites: | | | | |
|---|---|---|---|---|
| Curing Temperature (° C.) | [a]Td(5) in air | [a]Td(5) in $N_2$ | [b]C.Y. in air | [b]C.Y. in $N_2$ |
| 150 | 325 | 315 | 22.7 | 65.4 |
| 200 | 389 | 362 | 23.8 | 68.3 |
| 250 | 478 | 472 | 26.0 | 69.9 |
| 300 | 500 | 511 | 24.9 | 71.2 |
| 350 | 528 | 530 | 25.9 | 75.6 |
| 400 | 523 | 538 | 24.9 | 73.0 |

[a]Td(5) 5% mass loss temperature (° C.)
[b]C.Y. ceramic yield at 1000° C. (%)

Example 17
Synthesis of Polyimide Resins from OAPS and 3,3',4,4'-Benzophenonetetra-carboxylicdianhydride (BTDA)

Experimental: DMF (2.4 ml) solution of BTDA (0.224 g, 0.695 mmol) was added to a DMF (0.8 ml) solution of OAPhS (0.2 g, 0.173 mmol, N: 1.39 mmol) at room temperature. The mixture was added into an aluminum container and heated at 130° C. for 2 h and 350° C. for 4 h in nitrogen. The ramp rate was 5° C./min.

| Spectroscopic Data for OAPS/BTDA Nanocomposites: | |
|---|---|
| FT-IR ($cm^{-1}$) | 3070 ($\delta$C—H), 1785, 1727 ($\delta$C=O), 1374 ($\delta$C—N), 1120 ($\delta$Si—O), |
| TGA (air, wt % at 1000° C.) | 16.5 (20.9) |

Example 18
Synthesis of Nanocomposites with Core-Shell Structure
(Step 1)

To a 25 ml schlenk flask equipped with a condenser, OBrPS (0.5 g, 0.3 mmol, Br: 1.40 mmol), were added octa(vinyldimethylsiloxy)silsesquioxane (8.84 g, 7.21 mmol), tetraethylammonium chloride (0.398 g, 2.40 mmol) dicyclohexylmethylamine (0.772 ml, 3.60 mml) and palladium acetate (0.0108 g, 0.0480 mmol) with dry N,N-dimethylacetamide (10 ml) under nitrogen. The mixture was heated at 100° C. under nitrogen for 54 h. After cooled to room temperature, diethyl ether (10 ml) and water (10 ml) was added and the organic layer was separated by a separatory funnel and dried over sodium sulfate (~1 g). The solvent was removed under reduced pressure using a rotavapor. The product was purified by a silica column chromatography. The eluent was the mixture of hexane and ethyl acetate (starting from the ratio of 5 to 1 and 5 to 4 in volume). Yield 0.3 g (14.6%, FW=6589 based on $^1$H-NMR, the number of reacted bromo phenyl groups was 4.3 out of 8). The ceramic yield was calculated based on the conversion obtained by $^1$H-NMR.

| Spectroscopic Data: | |
|---|---|
| FT-IR (cm$^{-1}$) | 3062, 2966 ($\delta$C—H), 1600, 1410 ($\delta$C=C), 1093 ($\delta$Si—O), |
| TGA (air/wt %/1000° C.) | 63:1 (70.0) |
| TGA (N$_2$/wt %/1000° C.) | — |
| GPC | Mn = 8918, Mw = 15344, PDI = 1.721 |

Example 19
Synthesis of Nanocomposites with Core-Shell Structure (Step 2)

To a 25 ml schlenk flask equipped with a condenser were added the product from the step 1 (0.181 g, 0.0264 mmol, 0.793 vinyl groups), octa(hydrodimethylsiloxy) silsesquioxane (2.4 g, 2.38 mmol) and Pt(dcp) (4.0 mM toluene solution, 40 μm, 1.6×10$^{-7}$ mol) with 10 ml of distilled toluene under nitrogen. The mixture was heated at 100° C. for 41 h under nitrogen. The excess amount of octa(hydrodimethylsiloxy)silsesquioxane was separated by recrystallization in toluene. The number of octa(hydrodimethylsiloxy)silsesquioxane introduced to the shell was estimated from the result of GPC (Mn), which was 3.5 per the octa(vinyldimethylsiloxy)silsesquioxane in the shell.

| Spectroscopic Data: | |
|---|---|
| FT = IR (cm$^{-1}$) | — |
| TGA (air/wt %/1000° C.) | — |
| TGA (N$_2$/wt %/1000° C.) | — |
| GPC | Mn = 24265, Mw = 37966, PDI = 1.565 |

Example 20
Layer-by-Layer Deposition of a Single Monolayer of the Silsesquioxanes Prior to layer deposition, silicon wafers and glass substrates were cleaned in a piranha solution (3:1 H$_2$SO$_4$:H$_2$O$_2$) and rinsed with acetone, deionized water and methanol several times and dried over nitrogen flow. They were dipped in 5 vol % aminopropyltriethoxysilane (APTEOS) in toluene under nitrogen for 24 h and then rinsed with toluene and acetone several times to remove residual APTEOS and the floating gel formed by APTEOS.

APTMOS treated substrates were dipped in 10 wt % OG solution in toluene and dried in air flow. They were then cured at 150° C. under nitrogen for 24 h. After the curing, substrates were rinsed with boiling toluene and acetone several times to remove residual OG.

After OG deposition, the substrates were dipped in 10 wt % OAPS and dried in flow. They were then cured at 150° C. under nitrogen for 24 h. After the curing, substrates were rinsed with boiling toluene and acetone several times to remove residual OAPS.

Substrates were cleaned with acetone and alcohol extensively prior to measurement. About 50 μm of deionized water was dropped onto the surface and the vertical images of the substrate and the water was recorded with a video camera. The images right after the water dropping were taken and printed in still-mode using a picture editing software. The contact angles were read as follows:

| Substrate | Amine Layer | OG Layer | OA Layer |
|---|---|---|---|
| Contact Angle | | | |

Thermal Gravimetric Analysis (TGA): Thermal stabilities of materials under nitrogen were tested using a 2960 simultaneous DTA-TGA Instrument (TA Instruments, Inc., New Castle, Del.). Small samples (15–25 mg) were loaded in platinum pans and ramped to 1000° C. under N2 at 5° C./min. The N$_2$ flow rate was 60 ml/min.

Dynamic Mechanical Analysis (DMA): Dynamic mechanical behavior of cured samples were studied using a TA Instruments 2980 dynamic mechanical analyzer (New Castle, Del.). The cured samples were polished to 3.0 mm×12.0 mm×3.0 mm and mounted on the single cantilever clamp. The mechanical properties were measured under nitrogen in step mode every 10° C. at temperatures from −50° C. to 200° C. Prior to each measurement, the furnace was kept at room temperature under nitrogen.

Example 21
Imide Film Formation Using a Solvent

Octaaminophenylsilsesquioxane (OAPS) and pyromellitic dianhydride (PDA) (mole ratio of NH$_2$ in OAPS:anhydride in PDA=1:1, total 1 g) are dissolved in 10 ml of NMP and the solution is cast onto a glass slide. The solvent is evaporated under mild conditions (~40° C.) for one day. When the film becomes stable, it is placed in 300 ml of water in beaker and sonicated. The film is carefully peeled off and dried at room temperature. Then, it is slowly heated to and kept at 150° C. for 4 h, and at 300° C. for 2 h. Yellow to brown films (depending on time and thickness) are obtained.

Example 22
Copolyimide Films

Films obtained by example 21 are typically brittle but this can be reduced by co-imidization of OAPS and flexible linear amines. For example, octaaminophenylsilsesquioxane (OAPS), oxydianiline (ODA) and pyromellitic dianhydride (PDA) (mole ratio of NH$_2$ in OAPS+ODA:anhydride in PDA=1:1, varying amount of ODA, total 1 g) are dissolved in 10 ml of NMP and the solution is cast on to the glass slides. Following the same cure method described above, flexible dark yellow films are obtained.

Example 23
Synthesis and Processing of Imides by Melt Processing

Octaaminophenylsilsesquioxane (OAPS) and the tetraester pyromellate (TEP) (mole ratio of NH$_2$ in OAPS:ester in TEP=1:2, total 1 g) are weighed into a 20 ml vial and heated to 160° C. until the TEP melts. The mixture is stirred until it becomes homogeneous. It is then cast onto a surface and kept for 12 h at the same temperature under nitrogen. It is further post cured at 300° C. for another 4 h. Thicker films and cast shapes require longer times and slower heating rates. Fibers can be melt spun and either heated as they are drawn or in a post spinning process to fully cure.

Example 24
Copolyimides

Octaaminophenylsilsesquioxane (OAPS) and a linear diamine such as oxydianiline (ODA) and the tetraester pyromellate (TEP) (mole ratio of $NH_2$ in OAPS:ester in TEP=1:2, total 1 g) are weighed into a 20 ml vial and heated to 160° C. until the TEP melts. The mixture is stirred until it becomes homogeneous. Then, it is cast on a surface and kept for 12 h at the same temperature under nitrogen. It is further post cured at 300° C. for another 4 h. Thicker films and cast shapes require longer times and slower heating rates. Fibers can be melt spun and either heated as they are drawn or in a post spinning process to fully cure.

Example 25

Synthesis of Octa(acetylphenyl)silsesquioxane (AcOPS)

To a 500 ml schlenk flask under nitrogen gas, was placed of aluminum chloride (16.80 g, 126 mmol) with 100 ml of $CH_2Cl_2$ and 100 ml of $CS_2$. Acetyl chloride (8.26 ml, 116 mmol) was then added via syringe. The mixture was stirred at 0° C. under nitrogen for 15 min. OPS (10 g, 9.76 mmol, -Ph 78.1 mmol) was then added to the mixture with stirring and the solution was stirred at 0° C. for 5 h. To quench the reaction, 50 g of ice was added and the organic layer was extracted with 200 ml ethyl acetate. The organic layer was washed with water until the aqueous layer became pH=~7 and dried over sodium sulfate. The solvents were removed by rotoevaporation and 100 ml ethyl acetate added to the flask. The resulting suspension was filtered through a 1 cm Celite column. The yellow filtrate was then set aside, and the undissolved powder was dissolved in 100 ml $CH_2Cl_2$ and passed through the column. The $CH_2Cl_2$ layer was reduced by rotoevaporation to 20 ml, and precipitated dropwise into 750 ml of hexanes, which resulted in a white powder. The powder was collected by filtration, washed with hexane, and dried in vacuo. Yield 6.25 g (47.2%), 100% acylated (by $^1$H-NMR), meta/para=86/14 (by $^1$H-NMR). The ethyl acetate filtrate can also be reduced to ~20 ml and precipitated into 750 ml hexanes. After filtration and drying, this resulted in 5.54 g (42.7%) of off-white powder, 92% acylated (by $^1$H-NMR).

Example 26

Synthesis of Octa(a,a-dibromoacetylphenyl)silsesquioxane ($Br_2AcOPS$)

To a 25 ml schlenk flask under nitrogen gas was placed AcOPS (0.150 g, 0.876 mmol $COCH_3$) and 3 ml $CH_2Cl_2$. Bromine (0.462 g, 2.89 mmol) was added dropwise to the solution. A vigorous exothermic reaction normally results. If the reaction does not start on its own, gentle heating may be required to start the reaction, which then proceeds on its own. After 30 minutes, the solution was added to 10 ml $CH_2Cl_2$ in a separatory funnel, washed with 10% $NaHSO_3$ twice (to remove excess $Br_2$), and water three times. The $CH_2Cl_2$ layer was dried over sodium sulfate and then rotovapped to dryness. The material was dissolved in 3 ml $CH_2Cl_2$ and precipitated into 75 ml hexane. The product was collected by filtration and dried in vacuo. Yield 0.237 g (82.2%). Characterization: IR 1704 ($n_{C=O}$); $^1$H NMR ($CDCl_3$) d 6.55 (s, 1H, $CBr_2H$); TGA 19.3% (calc'd 18.3%)

Example 27

Synthesis of Poly(acetylphenyl)silsesquioxane (AcPPS)

To a 50 ml schlenk flask under nitrogen gas, was placed of aluminum chloride (0.838 g, 6.3 mmol) with 5 ml of $CH_2Cl_2$ and 5 ml of $CS_2$. Acetyl chloride (0.413 ml, 5.8 mmol) was then added via syringe. The mixture was stirred at 0° C. under nitrogen for 15 min. PPS (0.5 g, 0.484 mmol, -Ph 3.87 mmol) was then added to the mixture with stirring and the solution was stirred at 0° C. for 5 h. To quench the reaction, 20 g of ice was added and the organic layer was extracted with 50 ml ethyl acetate. The organic layer was washed with water three times, dried over $Na_2SO_4$, and passed through a 1 cm Celite column. After reduction by rotoevaporation to 5 ml, the yellow solution was precipitated into 75 ml hexane. Yield 0.338 g (52.3%)

Polyphenylsilsesquioxane can be acylated under the optimized conditions for OPS in moderate yields. Conversion of phenyl to acetylphenyl is 90% (as per 1H-NMR). It is interesting to note that the polydispersity and molecular weight of the PPS decreases significantly upon acylation. This phenomenon was also observed upon nitration of PPS, and can be explained by the cleavage of Si—O—Si bridges and subsequent rearrangement during the acidic synthesis and work-up.

Example 28

Synthesis of Octa(i-butyrl-phenyl)silsesquioxane (iButOPS)

To a 50 ml schlenk flask under nitrogen gas, was placed of aluminum chloride (0.838 g, 6.3 mmol) with 5 ml of $CH_2Cl_2$ and 5 ml of $CS_2$. Iso-butyrl chloride (0.630 ml, 5.8 mmol) was then added via syringe. OPS (0.5 g, 0.488 mmol, -Ph 3.9 mmol) was then added to the mixture with stirring and the solution was stirred at reflux for 10 h. To quench the reaction, 5 g of ice was added and the organic layer was extracted with 50 ml $CH_2Cl_2$. The organic layer was washed with water until the aqueous layer became pH=~7 and dried over sodium sulfate. The solvents were removed by rotoevaporation and 50 ml $CH_2Cl_2$ added to the flask. The resulting liquid was filtered through a 1 cm Celite column. The solution was reduced to ~10 ml, and precipitated dropwise into 100 ml of hexanes, which resulted in a white powder. The powder was collected by filtration, washed with hexane, and dried in vacuo. Yield 0.477 g (68 yield %), 75% conversion to $Ph-COC(CH3)_2H$ (by $^1$H-NMR).

Example 29

Synthesis of Octa(ethylphenyl)silsesquioxane (iButOPS)

To a 50 ml schlenk flask under nitrogen gas, was placed of aluminum chloride (0.838 g, 6.3 mmol) with 5 ml of $CH_2Cl_2$ and 5 ml of $CS_2$. Ethyl chloroformate (0.555 ml, 5.8 mmol) was then added via syringe. OPS (0.5 g, 0.488 mmol, -Ph 3.9 mmol) was then added to the mixture with stirring and the solution was stirred at reflux for 1 h. To quench the reaction, 5 g of ice was added and the organic layer was extracted with 50 ml $CH_2Cl_2$. The organic layer was washed with water until the aqueous layer became pH=~7 and dried over sodium sulfate. The solvents were removed by rotoevaporation and 50 ml $CH_2Cl_2$ added to the flask. The resulting liquid was filtered through a 1 cm Celite column. The solution was reduced to ~10 ml, and precipitated dropwise into 100 ml of hexanes, which resulted in a white powder. The powder was collected by filtration, washed with hexane, and dried in vacuo. Yield 0.397 g (69 yield %), 70% conversion to $Ph—CH_2CH_3$ (by $^1$H-NMR).

While embodiments of the invention have been illustrated and described, it is not intended that these embodiments illustrate and describe all possible forms of the invention. Rather, the words used in the specification are words of description rather than limitation, and it is understood that various changes may be made without departing from the spirit and scope of the invention.

What is claimed is:

1. A functionalized silsesquioxane, selected from the group consisting of octakis(aminophenyl)silsesquioxane, octakis(N-maleimidoaminophenyl)silsesquioxane, octakis(acetylphenyl)silsesquioxane, and octakis-(bromophenylsilsesquioxane).

2. A method of preparing functionalized silsesquioxane macromonomers comprising providing a phenyl-substituted silsesquioxane and substituting phenyl group(s) of said phenyl-substituted silsesquioxane with a reactive functional group or precursor thereof wherein said step of substituting comprises nitrating phenyl groups of said phenyl-substituted silsesquioxane to form a nitrophenyl-substituted silsesquioxane followed by reducing the nitrophenyl groups to aminophenyl groups to form an aminophenyl-substituted silsesquioxane.

3. In a process for the preparation of a functionalized silsesquioxane wherein a silica source is converted to polyanionic form employing a quaternary ammonium hydroxide, followed by reaction with a hydridoalkylchlorosilane to form a silsesquioxane bearing hydridosilyl-functional reactive groups, and optionally employing said silsesquioxane bearing hydridosilyl-functional reactive groups to hydrosilylate an unsaturated organic compound, the improvement comprising selecting as the silica source a silica source obtained from the combustion or calcination of silica-containing natural products.

4. The process of claim 3 wherein said silica source is one or more of fly ash or rice hull ash.

* * * * *